(12) United States Patent
Di Pierro

(10) Patent No.: US 7,476,392 B2
(45) Date of Patent: Jan. 13, 2009

(54) PHARMACEUTICAL AND/OR COSMETIC COMPOSITIONS FOR THE TREATMENT OF LOCALISED ADIPOSITIES AND CELLULITE

(75) Inventor: Francesco Di Pierro, Milan (IT)

(73) Assignee: Indena S.p.A., Milan (IT)

( * ) Notice: Subject to any disclaimer, the term of this patent is extended or adjusted under 35 U.S.C. 154(b) by 603 days.

(21) Appl. No.: 10/477,923

(22) PCT Filed: May 16, 2002

(86) PCT No.: PCT/EP02/05390

§ 371 (c)(1), (2), (4) Date: Nov. 18, 2003

(87) PCT Pub. No.: WO02/098436

PCT Pub. Date: Dec. 12, 2002

(65) Prior Publication Data

US 2004/0151786 A1     Aug. 5, 2004

(30) Foreign Application Priority Data

Jun. 5, 2001    (IT)   .......................... MI01A001182

(51) Int. Cl.
*A61K 8/02* (2006.01)
(52) U.S. Cl. .................................................... 424/401
(58) Field of Classification Search ................. 424/401; 514/860
See application file for complete search history.

(56) References Cited

U.S. PATENT DOCUMENTS

| | | | | |
|---|---|---|---|---|
| 5,104,655 A | * | 4/1992 | Bombardelli et al. | ......... 514/78 |
| 5,118,671 A | * | 6/1992 | Bombardelli et al. | ......... 514/26 |
| 5,194,259 A | | 3/1993 | Soudant et al. | |
| 5,514,374 A | * | 5/1996 | Bonte et al. | ................. 424/745 |
| 6,756,065 B1 | * | 6/2004 | Merizzi | ...................... 424/752 |

FOREIGN PATENT DOCUMENTS

WO      WO 01/19158      3/2001

OTHER PUBLICATIONS

Reilly W et al: "Body Contouring Using an Oral Herbal Antioxidant Formulation—Centelaplus: A Dose Controlled Observational Study" Redox Report, Churchill Livingstone, Edinburgh, GB, vol. 5, No. 2/3, 2000, pp. 144-145, XP000990069 ISSN: 1351-0002 the whole document.

Bombardelli E et al.: "Phytosomes in functional cosmetics." Fitoterapia, vol. 65, No. 5, 1994, pp. 387-401, XP001105302 ISSN: 0367-326X part "Effects on microcirculation".

Patent Abstracts of Japan vol. 1998, No. 12, Oct. 31, 1998 & JP 10 182473 A (Lion Corp), Jul. 7, 1998 abstract.

Bombardelli E et al: "Microvasculokinetic activity of ximenynic acid ethyl ester." Fitoterapia, vol. 65, No. 3, 1994, pp. 195-201, XP001104828 ISSN: 0367-326X p. 196, line 3—line 9; figure 3.

* cited by examiner

*Primary Examiner*—Sreeni Padmanabhan
*Assistant Examiner*—Renee Claytor
(74) *Attorney, Agent, or Firm*—Young & Thompson

(57) ABSTRACT

The present invention relates to pharmaceutical and/or cosmetic compositions containing a combination of the following active principles: a) complex of escin/beta-sitosterol with phospholipids, b) complex of *Gingko biloba* dimeric flavonoids with phospholipids, c) complex of *Centella asiatica* triterpenes with phospholipids, and optionally one or both of: d) ethyl ximeninate e) *Coleus forskolii* standardized extract.

4 Claims, No Drawings

PHARMACEUTICAL AND/OR COSMETIC COMPOSITIONS FOR THE TREATMENT OF LOCALISED ADIPOSITIES AND CELLULITE

The present invention relates to pharmaceutical and/or cosmetic compositions for the treatment of localised adiposities and cellulite.

Localised adiposities and cellulite affect a remarkable, increasing percentage of the western population, mainly women. Cellulite, in particular, also affects many normal weight-constitution, adult women without obesity problems. These problems are connected to panniculopathy conditions characterized by poor peripheral circulation, edema, fibrosis and altered lipocytes metabolism, therefore an ideal treatment should take into account all these factors.

The huge number of pharmaceutical or cosmetic formulations for the treatment of localised adiposities and cellulite currently available on the market have not so far solved satisfactorily the problem of localised adiposities and cellulite. Said compositions are generally based on active principles of vegetable origin, such as ivy, horse-chestnut, cola extracts; caffein, beta-adrenergic stimulants, methylxanthines, and the like. Nevertheless, none of said compositions has proved so far really effective, and the results obtained are often due to the dietetic regimen generally associated to said treatments, rather than to the use of said compositions.

It has now been found, and this is the object of the present invention, that pharmaceutical and/or cosmetic topical compositions containing a combination of active principles of vegetable origin provide excellent results in the treatment of localised adiposities and cellulite, drastically reducing cutaneous fat deposits and "orange-peel" skin, due to the combination of the different activities of the various components, which exert anti-edematous, antiphosphodiesterase, vasokinetic activities and promote collagen production.

The components of the compositions of the present invention are all known and used in pharmacy and/or in cosmetics, nevertheless it is to be noted that the activity of said single components, when used separately, is by far lower than that achieved with the compositions of the present invention; on the contrary, a synergistic effect among said various components is observed.

In particular, the present invention provides pharmaceutical and/or cosmetic topical compositions containing as active principles escin/beta-sitosterol complexes with phospholipids, *Gingko biloba* dimeric flavonoids complexes with phospholipids, ethyl ximeninate, *Coleus forskolii* extracts and *Centella asiatica* triterpenes complexes with phospholipids.

More particularly, the present invention relates to pharmaceutical and/or cosmetic compositions containing a combination of the following active principles:
 a) complex of escin/beta-sitosterol with phospholipids,
 b) complex of *Gingko biloba* dimeric flavonoids with phospholipids,
 c) complex of *Centella asiatica* triterpenes with phospholipids, and optionally one or both of:
 d) ethyl ximeninate,
 e) standardized *Coleus forskolii* extract.

According to a preferred embodiment of the present invention, the compositions of the present invention have the following percentage composition:
 a) complex of escin/beta-sitosterol with phospholipids: 0.1-2.5%;
 b) complex of *Gingko biloba* dimeric flavonoids with phospholipids: 0.1-2.5%;
 c) complex of *Centella asiatica* triterpenes with phospholipids: 0.1-2.5%, and optionally one or both of:
 d) ethyl ximeninate: 0.1-2.5%;
 e) *Coleus forskolii* standardized extract: 0.1-2.5%.

Escin is a saponin contained in horse-chestnut seeds, endowed with remarkable anti-edematous properties, probably due to a modification of the capillary permeability: it has in fact been shown that escin is capable of reducing the number and the diameter of the pores of the capillary walls through which water exchange occurs. Therefore, escin properties are considered useful in the treatment of the localised edematous conditions tipical of cellulite and of localised adiposities.

The complex of escin/beta-sitosterol with phospholipids, disclosed in EP 0 283 713, has the same action as escin, but shows a more prolonged release of the active principles and improved bioavailability.

The complex of *Gingko biloba* dimeric flavonoids with phospholipids, disclosed in EP 0 275 005, has the same activity as the dimeric *Gingko biloba* flavones in the free form, but shows a more prolonged release of the active principles and better bioavailability. *Gingko biloba* dimeric flavonoids are extremely potent vasoactive agents due to their inhibitory action on the release of histamine and of the enzyme cAMP phosphodiesterase from mast cells. The inhibition of this enzyme involves an increase in the level of cAMP, a molecule able to activate lipocytes metabolism. This complex therefore exerts a lipolytic action and improves the microvascular perfusion and the cutaneous trophism.

*Centella asiatica* triterpenes (asiatic acid, asiaticoside and madecassic acid) exert a beneficial action on the production of collagen (in the stable form) by dermal fibroblasts, by increasing the absorption of hydroxyproline, which is fundamental for collagen synthesis, thereby contrasting the cutaneous sclerosis responsible for the formation of the "orange-peel skin" typical of cellulite. The complex of *Centella asiatica* triterpenes with phospholipids disclosed in EP 0 283 713 provides prolonged release and better penetration in the dermis.

Ethyl ximeninate is the ethyl ester of ximeninic acid, a fatty acid which can be found in *Olax dissitiflora* and in other oleaginous plants of the genus *Ximenia*. Advanced capillaroscopic techniques have shown that ethyl ximeninate has a significant vasokinetic activity. This, combined with the activity of the other active principles of the formulation, is useful in the treatment of cellulite.

The standardized *Coleus forskolii* extract, described in example 1, contains forskolin, a well-characterized molecule able to stimulate adenylate cyclase activity and therefore to increase the concentration of cyclic nucleotides, molecules which stimulate lipolysis and haematic flow at microvascular level.

The compositions of the invention will be applied topically on body areas affected by localised adiposities and/or cellulite, for time periods ranging from some days to some months, depending on the severity of the disorder to be treated, with frequency of 1-2 applications a day.

The compositions of the invention will be formulated, according to conventional techniques, in the form of cream, oil, gel, foam, emulsion, milk and the like, optionally encapsulated in liposomes. Said compositions will contain the excipients conventionally used in pharmaceutical and/or cosmetic technology.

Examples of formulations are reported hereinbelow.

EXAMPLE 1

Preparation of a 20% Forskolin Standardized Extract of *Coleus forskolii*

1 kg of rhizomes and roots of *Coleus forskolii*, finely ground, are extracted using subsequently 10 l of $CO_2$ under continuous recycle, for 2 hours at a temperature of 45° C. and a pressure of 240 bars. After evaporation of the solvent at 50° C., the residue is dissolved in 5 volumes of hexane and back-extracted twice with 2 volumes of 90% v/v methanol.

The methanolic extract is concentrated to dryness to obtain 45 g of an extract containing 20% of forskolin.

EXAMPLE 2

Cream Formulation

| 100 g of cream contain: | |
|---|---|
| Complex of escin/beta-sitosterol with phospholipids | 1.50 g |
| Complex of *Centella asiatica* triterpenes with phospholipids | 0.50 g |
| Complex of dimeric *Ginkgo biloba* flavonoids with phospholipids | 0.50 g |
| *Coleus forskolii* standardized extract (20% forskolin) | 0.50 g |
| Ethyl ximeninate | 0.50 g |
| C12-C15 alkyl benzoate (Finsolv TN - Finetex) | 7.50 g |
| Cyclomethicon (Belsil CMO40 - Wacker) | 6.00 g |
| Ethoxydiglycole (Transcutol CG - Gattefosse) | 5.00 g |
| Glyceryl stearate and PEG-100 stearate (Arlacel 165 V-ICI) | 3.00 g |
| Karite butter (Shea butter) (Dekarite - Jan Dekker) | 3.00 g |
| Polysorbate 60 (Tween 60 - ICI) | 2.00 g |
| Cetyl alcohol | 1.00 g |
| Avocado oil (Avocado oil - Jan Dekker) | 1.00 g |
| Vitamin E acetate | 0.20 g |
| Ascorbyl palmitate | 0.10 g |
| Polyacrylamide (e) C13-14 isoparaffin (e) Laureth-7 (Sepigel 305 - Seppic) | 3.00 g |
| Imidazolidinylurea | 0.30 g |
| Methylchloroisothiazolinone (and) methylisothiazolinone (Kathon CG - Rohm & Haas) | 0.05 g |
| Bisodic EDTA | 0.10 g |
| BHT | 0.05 g |
| Perfume (162 - AGF) | 0.20 g |
| Depurated water | q.s. to 100 g |

The invention claimed is:

1. A composition, comprising:
   a) 1.50 g of a complex of escin/beta-sitosterol with phospholipids,
   b) 0.50 g of a complex of *Centella asiatica* triterpenes with phospholipids,
   c) 0.50 g of a complex of dimeric *Ginkgo biloba* flavonoids with phospholipids,
   d) 0.50 g of *Coleus forskolii* standardized extract (20% forskolin), and
   e) 0.50 g of ethyl ximeninate.

2. The composition as claimed in claim 1, wherein the extract of *Coleus forskolii* is a 20% forskolin standardized extract.

3. A method for the cosmetic treatment of localised adiposities and/or cellulite, comprising: applying an effective amount of a composition as claimed in claim 1 to said adiposities and/or cellulite.

4. A method for the cosmetic treatment of localised adiposities and/or cellulite, comprising: applying an effective amount of a composition as claimed in claim 2 to said adiposities and/or cellulite.

* * * * *